United States Patent [19]

Kleinerman

[11] Patent Number: 5,302,025
[45] Date of Patent: Apr. 12, 1994

[54] OPTICAL SYSTEMS FOR SENSING TEMPERATURE AND OTHER PHYSICAL PARAMETERS

[76] Inventor: Marcos Y. Kleinerman, 24 Jerome St., Southbridge, Mass. 01550

[21] Appl. No.: 654,809

[22] Filed: Feb. 13, 1991

Related U.S. Application Data

[60] Division of Ser. No. 711,062, Mar. 12, 1985, Pat. No. 5,004,913, which is a continuation-in-part of Ser. No. 608,932, May 14, 1984, Pat. No. 4,708,494, which is a continuation of Ser. No. 405,732, Aug. 6, 1982, abandoned.

[51] Int. Cl.⁵ .................. G02B 6/22; G01K 11/16
[52] U.S. Cl. .................. 374/131; 250/227.14; 374/161; 385/141
[58] Field of Search .............. 374/131, 161; 250/227.14; 385/141, 144

[56] References Cited

U.S. PATENT DOCUMENTS

| | | | |
|---|---|---|---|
| 3,615,312 | 10/1971 | Landry | 385/123 |
| 3,938,385 | 2/1976 | Horwath | 374/137 |
| 4,260,219 | 4/1981 | Greubel et al. | 385/141 X |
| 4,342,907 | 8/1982 | Macedo et al. | 374/131 X |
| 4,372,648 | 2/1983 | Black | 385/144 |
| 4,437,772 | 3/1984 | Samulski | 374/131 |
| 4,592,664 | 6/1986 | Bijlenga et al. | 374/131 |
| 4,673,299 | 6/1987 | Dakin | 374/131 |
| 4,708,494 | 11/1987 | Kleinerman II | 374/131 X |
| 4,823,166 | 4/1989 | Hartog et al. | 374/131 X |
| 4,834,496 | 5/1989 | Blyler, Jr. | 385/127 X |
| 5,004,913 | 4/1991 | Kleinerman I | 374/131 X |
| 5,052,820 | 10/1991 | McGinniss et al. | |
| 5,096,277 | 3/1992 | Kleinerman | 385/12 |

Primary Examiner—Daniel M. Yasich

[57] ABSTRACT

Optical sensors for physical parameters use a parameter-dependent relative distribution of the intensity of interrogating light of wavelengths $\lambda_1$ between two light-guiding regions of a light-guiding probe. The relative distribution can be determined by a plurality of means including the spatial separation of the lights carried by the two light-guiding regions, and/or the conversion of one of the lights into light of wavelengths $\lambda_2$ different and easily separable from light of wavelength $\lambda_1$. The sensors can be adapted to measure diverse physical parameters, including but not limited to temperature, and to measure infrared radiation by measuring its heating effect on the sensing probes.

19 Claims, 6 Drawing Sheets

OPTICAL SYSTEMS FOR SENSING TEMPERATURE AND OTHER PHYSICAL PARAMETERS

CROSS-REFERENCE TO RELATED APPLICATIONS

This is a division of application Ser. No. 711,062 filed Mar. 12, 1985, (now U.S. Pat. No. 5,004,913), which in turn is a continuation-in-part of application Ser. No. 608,932 filed May 14, 1984 (now U.S. Pat. No. 4,708,494), which in turn is a continuation of application Ser. No. 405,732 filed Aug. 6, 1982, now abandoned. The specification of U.S. Pat. No. 5,004,913 is incorporated by reference herein in its entirety.

BACKGROUND OF THE INVENTION

The present invention relates to improved methods and devices for sensing temperature and other physical fields, based on the effect of the physical field on the relative distribution of the intensity of interrogating light between two distinct components of an optical light guide. The physical fields covered by this invention include, in addition to temperature, anything which can cause a change in said relative distribution, including infrared radiation and the spatial distribution thereof.

The term "thermal sensing" as used in this application has a broad coverage. It covers the sensing of a thermal condition, like temperature, or any agent or process which can produce a temperature change, including as examples infrared radiation and exothermic chemical reactions.

DESCRIPTION OF THE PRIOR ART

Prior art methods and devices for measuring temperature include the use of probes made of materials having temperature-dependent photo-luminescence properties. One of the earliest systems was described in U.S. Pat. No. 2,551,650 of Urbach, and used a photo-luminescent material the luminescence intensity of which was quenched appreciably with an increase of temperature. Luminescence quenching is usually associated with a decrease of the luminescence decay time of the material following excitation of its luminescence by pulsed or oscillatory light of wavelengths within an electronic absorption band characteristic of the material. Since the measurement of a luminescence decay time is usually more accurate and reliable than the measurement of a luminescence intensity (especially in the absence of intensity referencing), some recent temperature measurement techniques using photo-luminescent probes have used the temperature-dependent luminescence decay time as temperature indicator. These decay time techniques were used in a plurality of fiber optic temperature measuring techniques, including among others those described in U.S. Pat. Nos. 4,223,226 and 4,245,507 and in a publication by J. S. McCormack (*Electronics Letters* 17, 630 [1981]). These prior art techniques have, however, a serious disadvantage: As temperature increases, the signal strength and, hence, the measurement accuracy, decrease. This limits severely the temperature range of operation of probes which have a temperature coefficient of decay time of the order of one percent or better, so a wide temperature range can be achieved only with probes having a significantly lower temperature coefficient of decay time and, hence, a significantly lower sensitivity and accuracy.

Other prior art techniques for the optical measurement of temperature include the measurement of the temperature-dependent changes of the spectral distribution of the luminescence of some phosphors, as described in U.S. Pat. Nos. 3,639,765 and 4,061,578, among others.

None of the above techniques are suitable for measuring small temperature changes of the order of $10^{-2}$ kelvins (K) or smaller, as such measurements would require the capability of measuring minute changes of light intensity with an accuracy better than one part in 10,000.

The sensing of infrared radiation is most commonly carried out by electrical sensors. Two main kinds of sensors are: (a) quantum detectors, and (b) thermal detectors. The quantum detectors operate by converting a number N of infrared photons incident on the active surface of the detector into a number qN of free charges (electrons or "holes"), where q is the quantum efficiency of the detector. By contrast, the thermal detectors are essentially electrical temperature sensors which respond to the temperature rise of the active surface of the detector caused by the absorption of the infrared radiation.

There are also infrared sensors which are entirely optical. They are far less common than the electrical sensors, and are used in specialized applications. They also comprise quantum detectors and thermal detectors. The quantum detectors typically require a two-step excitation process, wherein a relatively high energy optical "pump" beam excites the molecules or atoms of the detector to an intermediate excited level. Then the infrared photons to be detected further excite these molecules or atoms to a higher energy level, from which they decay to the ground level by emission of visible radiation. The intensity of the emitted visible radiation is then an indicator of the intensity of the infrared radiation.

The optical thermal detectors include, for example, the rare earth-doped luminescent materials subject of U.S. Pat. Nos. 3,639,765 and 4,061,578. These infrared detectors of low thermal mass which are activated by ultraviolet or short wavelength visible radiation and emit luminescence light, the spectral distribution of which is a sensitive function of temperature. The infrared radiation is detected by the temperature increase caused by the absorbed infrared radiation, and its modulation of the sensor luminescence.

It is an object of this invention to provide methods and devices for sensing temperature, based on new ways of using the temperature-dependence of the index of refraction of at least one component of a light-guiding probe.

It is another object of this invention to provide a new technique whereby said temperature dependence of the index of refraction of the component of a light guide can be used for measuring minute temperature changes, suitable for measuring changes of the order of $10^{-3}$ kelvins or smaller.

Still another object of the present invention is to provide new methods and devices whereby said temperature dependence of the index of refraction of the component of a light guide can be used for sensing thermal infrared radiation and/or for converting a thermal infrared image into a visible image.

The techniques of this invention are also suitable for measuring other physical parameter besides thermal parameters, for example mechanical forces and any other fields which can affect the relative distribution of light between two regions of a light guide. Thus, another object of this invention is to provide systems for sensing said parameters and/or fields.

Other objects of the present invention will in part be apparent from the following discussion and will in part appear hereinafter.

SUMMARY OF THE INVENTION

As stated above, the objects of this invention are accomplished by the use of light guides including at least one material having an index of refraction which is a sensitive function of temperature. The propagation of visible or short wavelength infrared light at any point along the light guide is strongly dependent on the temperature of that point. Temperature changes within the light guide can be caused by heat conduction to or from an object or environment, including convective heat transfer via a fluid, or by radiation to or from a body or environment. The absorption of thermal infrared radiation, for example, increases the temperature of the light guide at the point where absorption occurred, causing a fraction of the intensity of the visible (or short wavelength infrared) light propagating along the light guide to be ejected from it, the intensity of the ejected light varying as a function of the temperature increase and, hence, of the intensity of the thermal infrared radiation absorbed by the film at that point.

DEFINITIONS

Within the context of this application, I am using the following definitions:

Light: optical radiation, whether or not visible to the human eye.

Luminescence: Light emitted by a material upon absorption of light or other radiation of sufficient quantum energy. The term includes both fluorescence and phosphorescence.

Photoluminescence: Luminescence generated by the absorption of light.

Luminescence centers: atoms or molecules (including ions) of a luminescent material which absorb excitation light and emit luminescence light.

Luminescence quantum efficiency (also referred to as luminescence efficiency): the ratio of the number of luminescence photons emitted by a luminescent material to the number of photons of the excitation light absorbed by the material.

Luminescence decay time, $\tau$: the time after the cessation of the excitation radiation in which the intensity of the luminescence decays from $I_o$ to $I_o/e$, where e is equal to 2.71828 and $I_o$ is the luminescence at any reference time chosen as "zero" time.

Physical variable: any physical property whose magnitude can change. Examples: temperature, pressure, flow rate, position, liquid level, and the like.

Physical parameter: physical variable.

Interrogating light: illuminating light injected into an optical probe for the physical variable.

Excitation light: illuminating light which can generate luminescence in a luminescent material.

Light beam: light being propagated through an optical system, including light propagating along optical fibers, regardless of degree of divergence.

Light-guiding region of an optical fiber: a region of the fiber within which interrogating light can be transmitted at least in part in a direction along the fiber length. Examples: a fiber core, and any optically homogeneous cladding, whether or not having a light absorbing material dissolved therein.

Cladding: a light-guiding region surrounding a fiber core, whether or not in physical contact with the core and having a thickness no smaller than an optical wavelength, and regardless of the value of its index of refraction.

Proximal end (first end) and distal end of an optical fiber: the end into which interrogating light is launched (injected) is the proximal end. The other end is the distal end.

DETAILED DESCRIPTION OF THE INVENTION

The physical processes involved in the invention include the redistribution of the intensity of the interrogating light between two light-guiding regions of an optical light guide, caused by changes of the index of refraction of at least one of said regions in response to changes in the magnitude of a physical parameter. These processes can be used for constructing a number of devices for a plurality of applications. Examples of embodiments of such devices are described in the following sections.

New Fiber Optic Sensors Based on Core/Cladding Light Redistribution

Figure 1:
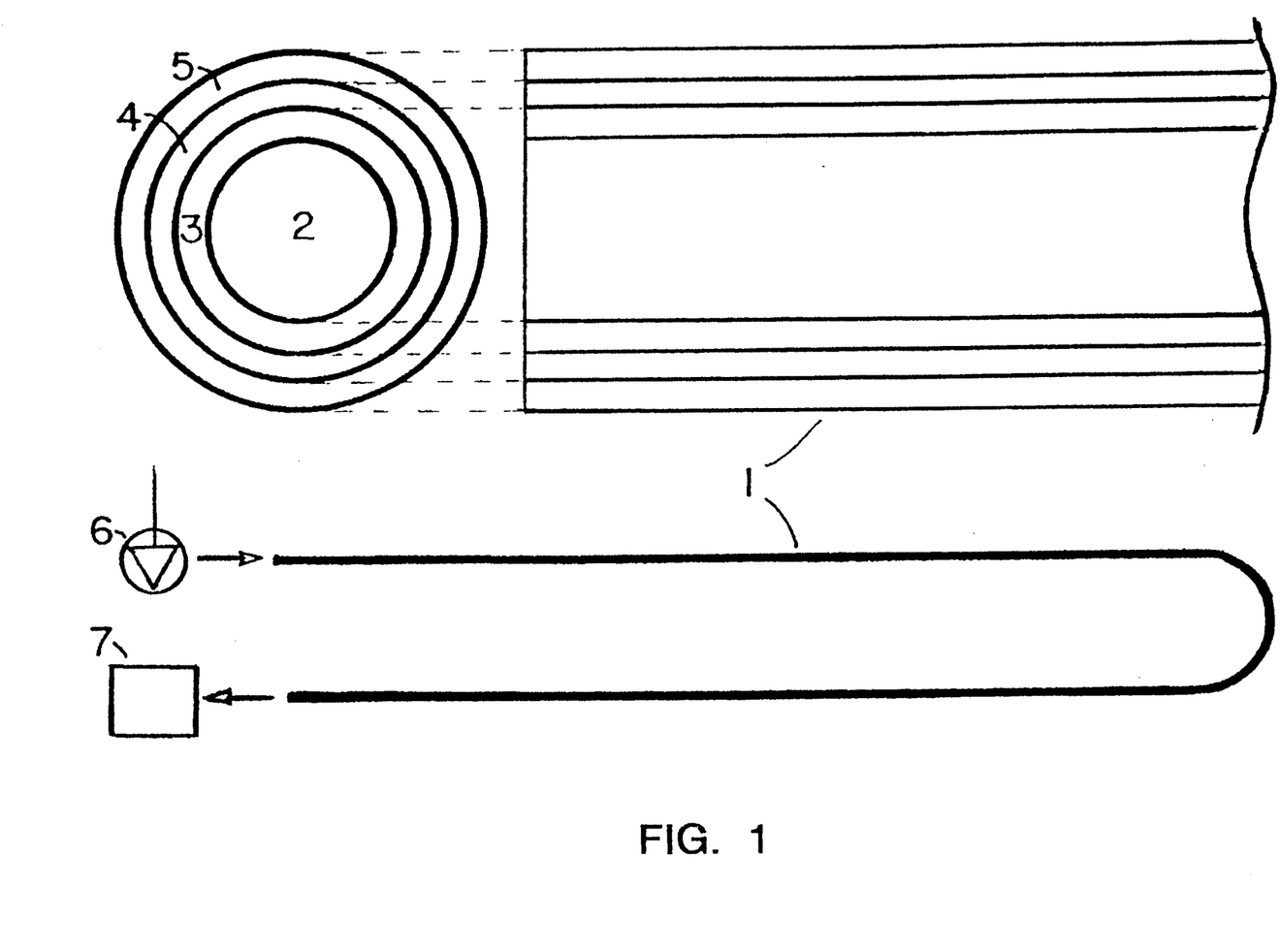
FIG. 1 illustrates an optical fiber including a luminescent cladding, suitable for sensing changes in the magnitude of a physical parameter according to this invention.

FIG. 1 illustrates an embodiment of a new system, based on the present invention, for measuring the ratio of the intensity of the core modes to that of the cladding modes in an optical fiber. The system uses as a sensing probe an optical fiber 1 having a clear core 2 with an index of refraction $n_1$, a clear cladding 3 having an index of refraction $n_2$ lower than $n_1$, a second cladding 4 with an index of refraction $n_3$ not lower than $n_2$ and having dissolved therein a photoluminescent solute which will absorb at least part of the fraction of the intensity of the interrogating light beam injected into the core which is coupled to the cladding under the action of a physical variable, and an outer cladding 5 with an index of refraction $n_4$ lower than $n_2$. The system works as follows:

A light source 6 launches (injects) an interrogating light beam of wavelengths $\lambda_1$ into the fiber core 2. The variable physical field (variable) F being sensed causes a change in the magnitude of the fraction of the intensity of the interrogating light injected into the core 2 which is deflected into cladding 4 through cladding 3.

This causes a change in the intensity of the luminescence light of wavelengths $\lambda_2$ generated at the cladding 4. Both the undeflected interrogating light and a fraction of the intensity of the luminescence light are directed to the photodetection station 7 where the two lights are measured by techniques known in the art. The relative intensities of these two lights are an indicator of the magnitude of the physical variable F acting on the fiber.

Cladding 4 can be a glass doped with an inorganic photoluminescent ionic species or an organic polymer doped with a fluorescent dye. Examples of inorganic photoluminescent specie are trivalent chromium and trivalent rare earth ions selected from the group comprising neodymium, ytterbium, erbium, samarium, holmium, thulium and europium. There is a very large number of fluorescent dyes which can be dissolved in the organic polymer constituting cladding 4. Dyes which can be excited with available light-emitting diodes (LEDs) or laser diodes (LDs) include, for example, those of the bis-benzanthrone family of dyes, for example Vat Green 1.

A Simple Fiber Optic Thermometer

Figure 2:
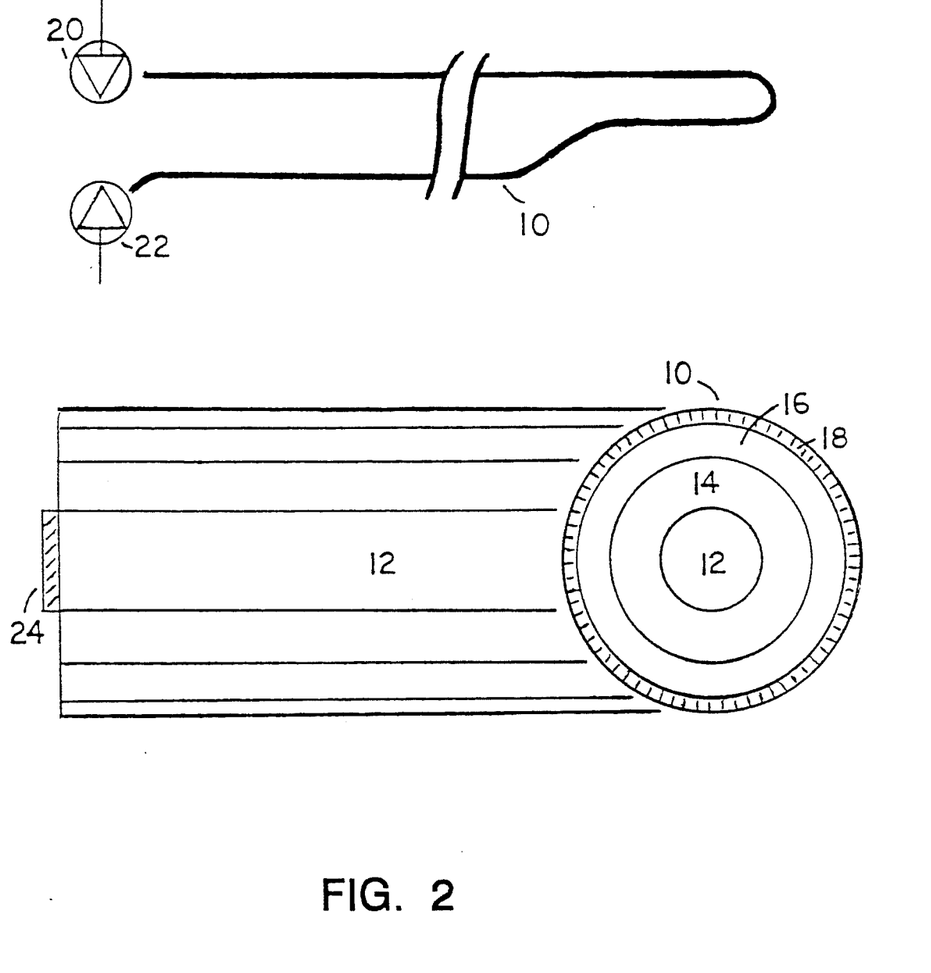
FIG. 2 illustrates an optical fiber having two polymeric claddings, used as a temperature probe according to this invention.

An embodiment of a thermometer according to this invention is illustrated in FIG. 2. It uses as a probe an optical fiber 10 including a glass core 12 having an index of refraction $n_1$, and two concentric plastic claddings. The first cladding 14 immediately surrounding the core has an index of refraction $n_2$ lower than $n_1$. The second cladding 16 around the first cladding has an index of refraction $n_3$ lower than $n_2$. The temperature coefficients of $n_2$ and $n_3$ are approximately equal, and substantially greater than the temperature coefficient of $n_1$. Cladding 16 is covered by a black or otherwise light-absorbing coating 18. The numerical apertures $(NA)_1$ and $(NA)_2$ of core 12 and cladding 14, respectively, are given by the relations $$(NA)_1 = (n_1^2 - n_2^2)^{\frac{1}{2}} \qquad (1)$$

and $$(NA)_2 = (n_2^2 - n_3^2)^{\frac{1}{2}} \qquad (2)$$

Since the value of $n_2$ decreases with increasing temperature at a much higher rate than the change of the value of $n_1$, the value of $(NA)_1$ increases substantially with increasing temperature. In most inorganic glasses, including silica, the value of $n_1$ changes so little with increasing temperature compared to index changes of plastics, that it may be regarded as essentially constant for the purposes of this description. Thus, the value of $(NA)_2$ is regarded as essentially invariant.

In operation, the fiber is bent at its sensing point, to fill the numerical aperture of both core 12 and cladding 14 when interrogating light is launched into the fiber by the light source 20. The distribution of the intensity of the interrogating light between the core 12 and the cladding 14 will be determined uniquely by the fiber temperature at the bend. Since $(NA)_2$ is substantially independent of temperature, the total light intensity arriving at the fiber distal end will not vary significantly with temperature, but the fraction of this intensity propagating along the first cladding at the fiber distal end will be a unique function of the temperature difference between the fiber distal end and its sensing point. Thus, if the temperature of the fiber distal end is controlled or just known, the probe temperature can be easily determined by measuring the intensity of the cladding light by photodetector 22 located at the fiber distal end. The core light is filtered out by miniature optical filter 24. It should be obvious to those of ordinary skill that, since the total light intensity arriving at the fiber distal end does not vary significantly with temperature, a measurement of the intensity of the light in cladding 14 indicates the intensity of the light propagating along the core, so the same probe temperature will be obtained by measuring the intensity of the core light instead of the cladding light.

A Distributed Temperature Sensor Using a Single Optical Fiber Probe

If the optical fiber 10 of FIG. 2 is made sufficiently long it can be used to measure temperature at a plurality of points distributed along its length, by using optical time domain reflectometry (OTDR) techniques. This is explained with reference to FIG. 3. An opaque coating 26 (for example an aluminum film) is applied to the face of the two claddings at the launch end of the fiber, so that the interrogating light can be launched only through core 12. The interrogating light is launched as a recurrent train of short pulses with a duration of the order of a few nanoseconds (ns) or shorter, depending on the spatial resolution desired (approximately 10 ns per fiber meter), over an acceptance angle $\theta$ for meridional rays necessary to fill the numerical aperture $(NA)_2$. In other words, the interrogating light fills both light-guiding regions 12 and 14. The value of $n_2$ decreases in a known manner with an increase in temperature at a much higher rate than the decrease in the value of $n_1$, and the intensity distribution of the interrogating light pulses between regions 12 and 14 will be determined by the relative magnitudes of $(NA)_1^2$ and $(NA)_2^2$.

Figure 3:
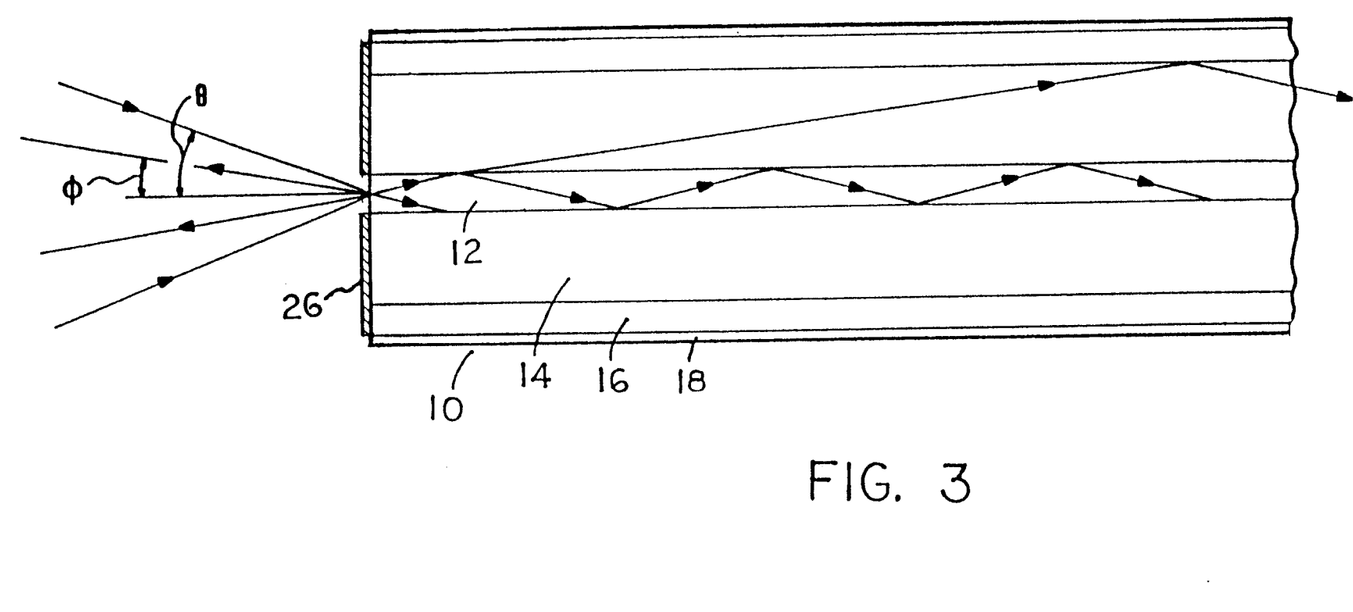
FIG. 3 illustrates an optical fiber probe for measuring distributed temperatures according to the invention.

Now, the intensity of the light pulses Rayleigh-backscattered from core 10 at any resolvable segment of the fiber, corrected for the intrinsic light attenuation of the fiber per unit length, will be a known function of the temperature of that segment.

In contrast to prior art methods of temperature measurement based on a temperature-dependent index of refraction, crosstalk between different sensing points is minimized by virtue of the fact that light rays deflected out of core 12 by a temperature change are not 'thrown away' as in the prior art, but are captured and returned to the region comprising core 12 and first cladding 14, thus restoring a temperature-dependent light distribution at every resolvable segment of the fiber.

Since the cladding faces of the fiber at the launch end are aluminized (or otherwise made opaque), and the diameter of cladding 14 can be made much larger than that of core 12, the intensity of the Rayleigh-backscattered light collected at the core launch end from any resolvable segment of the fiber will be proportional to the intensity of the interrogating light propagating within the core along that segment, determined by the magnitude of $(NA)_1$ and, hence, by the temperature-dependent value of $n_2$. Any contribution from cladding 14 to the collected Rayleigh-backscattered light can be further minimized by using a small collection angle $\phi$ consistent with the signal intensity needed. Since the total intensity of the light backscattered from a sensing point does not vary significantly with its temperature, a measurement of the intensity of the light in core 12 indicates the intensity of the light propagating along cladding 14, so the same temperature will be obtained by measuring the intensity of the cladding light instead of the core light.

The sensitivity and performance of the distributed temperature sensor depends on the materials used for the plastic cladding 14. For example, if the values of $(NA)_1$ and $n_2$ are about 0.15 and 1.450, respectively, at the ambient temperature of 300K, and the temperature coefficient of $n_2$ is about $2 \times 10^{-4}$ per kelvin at this temperature, then a temperature change of 1 kelvin will produce a change in the intensity of the light Rayleigh-backscattered from core 12 of approximately 2.5 percent, a relatively large change compared to prior art fiberoptic temperature sensing systems.

In a variation of the above technique, the second cladding 16 has dissolved therein a fluorescent dye at a concentration small enough not to alter significantly the temperature-dependent distribution of the interrogating light modes between the core 12 and the first cladding 14, but sufficient to generate fluorescence light pulses at the evanescent region of an intensity comparable to that of the Rayleigh-backscattered pulses from cladding 14. The intensity of the fluorescence light pulses is then indicative of the intensity of the modes of the interrogating light propagating along cladding 14. This variation has the advantage that one can measure simultaneously both the intensity of the core modes and that of the cladding modes, by Rayleigh backscattering and by fluorescence, respectively. An example of a suitable device for these measurements is described in the following paragraph, with the aid of FIG. 4.

Figure 4:
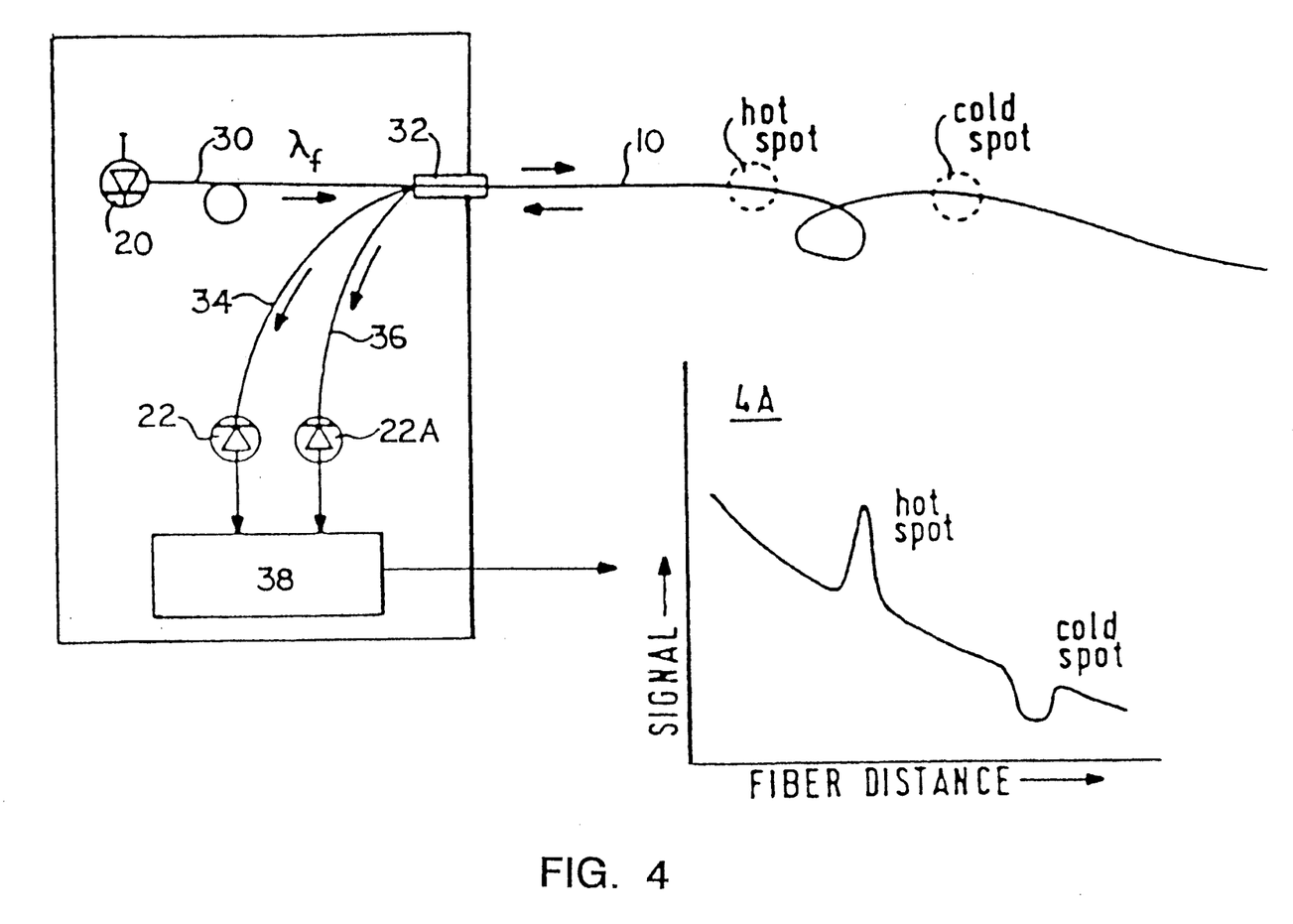
FIG. 4 illustrates a device for measuring distributed temperatures according to the invention.

Referring to FIG. 4, the light source 20 is driven to generate interrogating light pulses of a duration of the order of 10 ns and a wavelength $\lambda_f$. These light pulses are injected into the fiber segment 30 and, through the optical fiber coupler 32, into the core of the temperature-sensing fiber 10. At any point along the fiber, each interrogating light pulse generates a fluorescence light pulse of an intensity determined by the fiber temperature at that point, and a reference light pulse which is the Rayleigh backscatter of the interrogating light pulse. The intensities of these two pulses captured within the fiber are back-transmitted by the optical fiber to the coupler 32 and, via optical fiber segments 34 and 36, to photodetectors 22 and 22A, respectively. The time of arrival of these two pulses at the photodetectors, relative to the time of injection of the interrogating light pulses into the fiber 10, identifies the location of the temperature sensing point. The relative intensities of these two back-transmitted pulses, processed by the microprocessor 38, are an indicator of the fiber temperature at the sensing point.

A Differential Fiber Optic Thermometer

Figure 5:
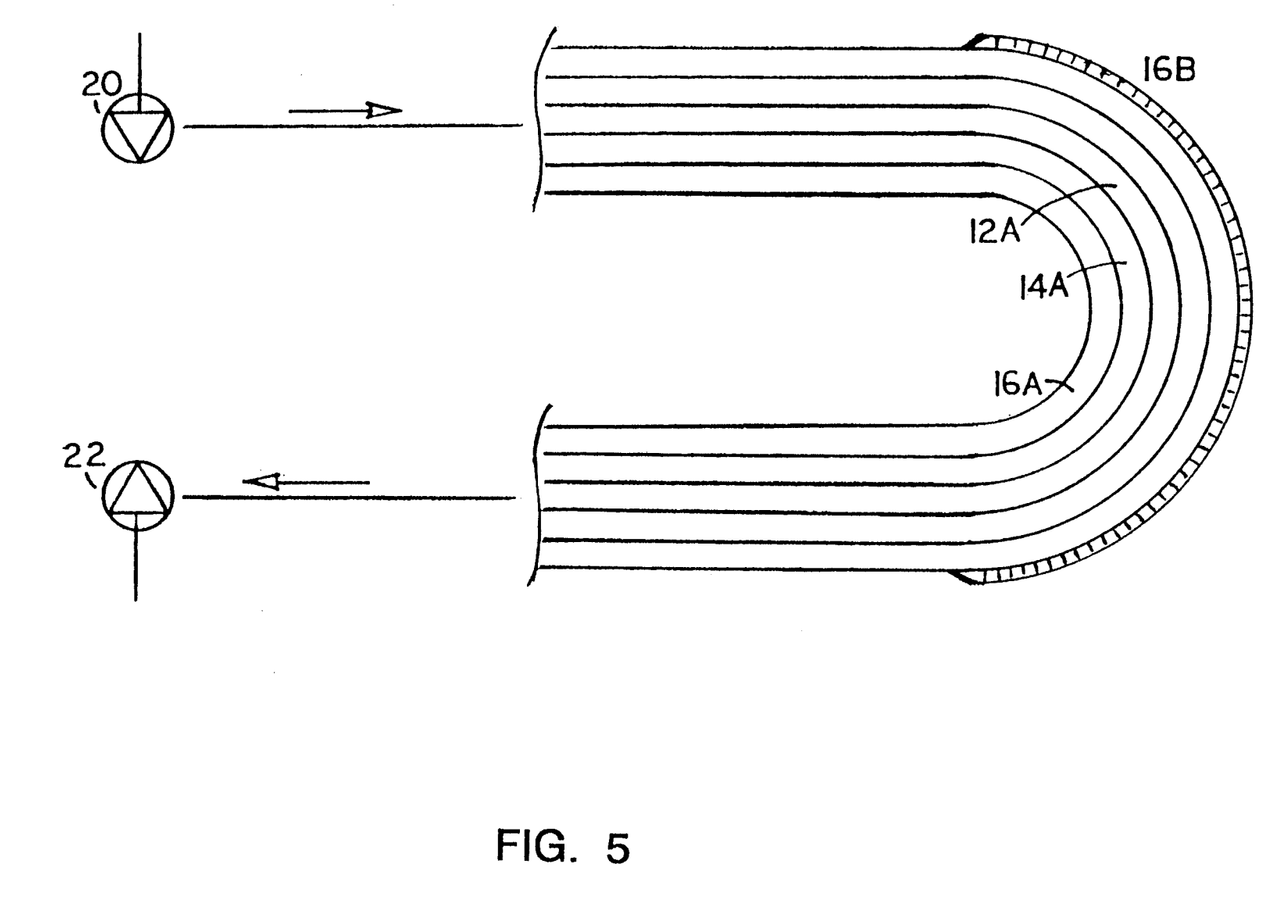
FIG. 5 shows a differential fiber optic thermometer according to this invention.

One preferred embodiment of the differential fiber optic thermometer is described with reference to FIG. 5. The probe is a multimode optical fiber 10A having a glass core 12A with an index of refraction $n_1$, and a clear elastomeric plastic cladding 14A with a thickness not greater than about 5 micrometers and an index of refraction $n_2$ lower than $n_1$ and which decreases with increasing temperature at a much higher rate than any change of the value of $n_1$. Around this cladding there is a second cladding 16A having a fluorescent dye dissolved therein and an index of refraction $n_3$ not lower than $n_2$. A short segment of this fiber exposed to the temperature to be measured has a black coating 16B on cladding 16A, to 'strip' the fluorescence cladding modes. Outside this segment, the fluorescent cladding 16A is covered with a transparent outer cladding 17 having an index of refraction $n_4$ lower than $n_2$. Within the segment of the fiber exposed to the temperature to be measured there is a bend designed to make the interrogating light launched by light source 20 fill the numerical aperture $(NA)_1$ of the fiber core. Because of the bend on the fiber, a substantial fraction of the intensity of the interrogating light launched into the fiber core is deflected to the fluorescent cladding, where it generates fluorescence light with an intensity proportional to the intensity of the deflected fraction. The black coating 16B 'strips' (removes) this fluorescence light from the fiber. Now, if the temperature of the exposed segment increases to $T_1$ relative to the fiber temperature $T_0$ just outside the segment in the direction of propagation of the interrogating light, the fraction of the intensity of the interrogating light deflected into the fluorescent cladding within said segment decreases as the numerical aperture of the fiber increases from $(NA)_{10}$ to $(NA)_{11}$. Thus, the intensity of the interrogating light propagating along the core 12A increases from $I_0$ to $(I_0 + \Delta I)$. But as the interrogating light reaches the region of temperature $T_0$, the intensity increase $\Delta I$ is lost to the fluorescent cladding as the numerical aperture of the fiber core decreases to $(NA)_{10}$ from $(NA)_{11}$, there generating a fluorescence light with an intensity proportional to $\Delta I$.

This device is particularly suitable for monitoring exothermic chemical reaction, and as such can be used in enzymatic biochemical analysis.

It should be apparent to a person having at least average competence in the art that an optical fiber probe having a fluorescent cladding around a clear core can be used for sensing other physical parameters besides temperature. Any physical change which can cause the deflection of interrogating light from the core to a luminescent cladding, or affect the extent of said deflection, is measurable with such probe.

The Sensing of Thermal Infrared Radiation

Figure 6:
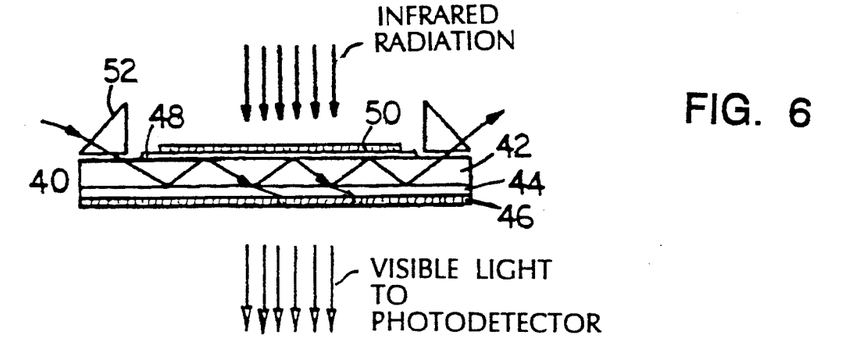
FIG. 6 illustrates an arrangement for sensing infrared radiation according to the invention.

An embodiment of a device for sensing infrared radiation is described with reference to FIG. 6 (similar to FIG. 4 in the parent application Ser. No. 711,062 now U.S. Pat. No. 5,004,913), which illustrates one of the preferred embodiments of the invention. A thin film probe 40 comprises a light-guiding layer 42 preferably less than 10 micrometers thick, made of a material having an index of refraction $n_1$ with a relatively large negative temperature coefficient of the order of $10^{-4}$ per kelvin or greater, is in optical and mechanical contact with a transparent second layer 44 having an index of refraction $n_2$ lower than $n_1$, the temperature coefficient of $n_2$ being lower than that of $n_1$. A white light-scattering coating 46 is applied to the outside of layer 44. On its other surface layer 42 is in contact with a thin transparent layer 48 having an index of refraction $n_3$ lower than $n_2$, and having in turn a thin infrared absorbing coating 50 applied on it. A visible light beam of wavelengths $\lambda_1$ is coupled to light-guiding layer 42 by means of prism 52, in such a manner as to couple into layer 42 all the light modes which the light-guiding layer can support. The beam propagates along the layer 42 by total internal reflection from layers 44 and 48, and with a number of angular modes which is a positive function of the magnitude of the numerical aperture $(NA)_p$ of the film probe, given by the relation $(NA)_p = (n_1^2 - n_2^2)^{\frac{1}{2}}$. When infrared radiation is absorbed by coating 50 at any point along the film probe, the probe temperature increases at that point, and the magnitude of $(NA)_p$ decreases. This causes a fraction of the intensity of the visible light propagating along layer 42 at that point to be deflected out of this layer. The deflected light is directed to a photodetector, generating an electrical signal therein, the magnitude of which is an indicator of the intensity of the infrared light incident on and absorbed by the light guide.

In an alternate embodiment, the light-scattering coating 46 may be replaced by a fluorescent coating which absorbs the light deflected from the film and converts it into luminescence light including wavelengths $\lambda_2$.

An Infrared Image Converter

Figure 7:
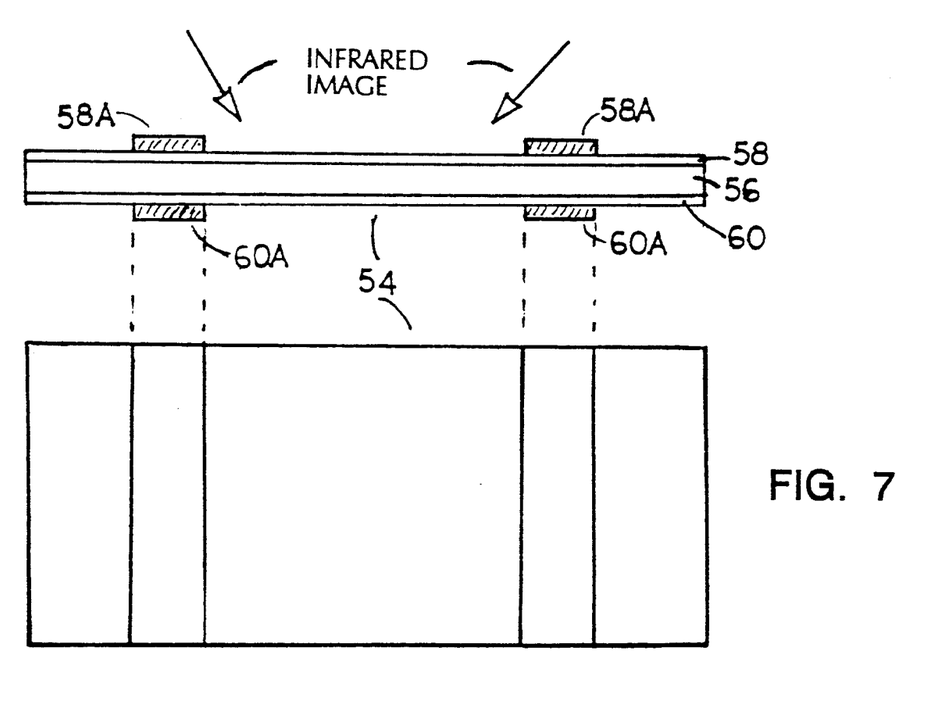
FIG. 7 shows an arrangement for converting a thermal infrared image into a visible image according to the invention.

The physical principles described in the preceding paragraphs can be applied to convert infrared images into visible images. One obvious way is to use scanning mirrors for sequentially focusing each resolvable element of the infrared image into the infrared sensing light guide used as a point detector. A more powerful technique uses a two-dimensional infrared sensing light guide in an arrangement described as follows, with reference to FIG. 7:

Referring to FIG. 7, the probe 54 is a two-dimensional film comprising a layer 56 having an index of refraction $n_1$, 'sandwiched' between layers 58 and 60. Light-guiding layer 56 differs from light guiding layer 42 of FIG. 6, and layers 58 and 60 differ respectively from layers 44 and 48 of the same figure, only in that they have a greater area, suitable for focusing a thermal image into the film probe. Their indices of refraction and the temperature dependence of these indices are the same. Layers 58 and 60 are painted black outside the area into which the infrared image is focused. Layer 58 is coated with the light-scattering layer 62. In operation, light of wavelength $\lambda_1$ is injected into layer 56 uniformly from one or, preferably, two or more square sides. The injected light has an angular distribution such as to overfill its numerical aperture $(NA)_{56}$ defined by the relation: $(NA)_{56} = (n_1^2 - n_2^2)^{\frac{1}{2}}$.

The light rays having angles smaller than the critical angle $\theta_c$ for total internal reflection (referenced to the normal to the plane of the film) enter layer 58 and are 'stripped' by the black stripes 58A and 60A on layers 58 and 60. The light rays having an angle greater than $\theta_c$ will propagate inside light guide 56 by total internal reflection at the boundaries between layer (light guide) 56 and layers 58 and 60. The thermal infrared image to be processed is focused into the film probe 54 by means of the focusing arrangement 64, which can be a lens system or a focusing mirror arrangement well known in the art. At any point where the incident infrared radiation raises the temperature of the film, a fraction of the intensity of the light of wavelength $\lambda_1$ propagating within light guide 56 will be deflected out of the light guide through layer 58 into layer 62, where it is converted into an image of wavelength $\lambda_1$. This image is then converted into a TV-type display by means of a TV camera.

In a variation of the above arrangement, layer 62 is replaced by a plastic film having a fluorescent dye dissolved therein. The dye is chosen so that it absorbs at least part of the intensity of the light of wavelength $\lambda_1$ deflected from the light guide 56 and converts it into fluorescence light emitted from the film probe. The thermal infrared image is thus converted into a fluorescence light image, which can be converted into a TV display by a standard TV camera.

Since certain changes may be made in the foregoing specification without departing from the scope of the invention herein disclosed, it is intended that all matter contained in the above description and/or depicted in the accompanying drawings be construed in an illustrative and not in a limiting sense.

I claim:
1. An optical fiber comprising a core having an index of refraction $n_1$ and at least one light-guiding region including a light-absorbing organic material, said material capable of absorbing light of pre-selected wavelengths $\lambda_1$ to which the core is substantially transparent.

2. An optical fiber as claimed in claim 1 wherein said light-guiding region is a cladding around said core and having an index of refraction lower than $n_1$.

3. An optical fiber as claimed in claim 2 wherein said cladding is fluorescent and includes a fluorescent dye incorporated therein which emits fluorescence of wavelengths including $\lambda_2$ different from $\lambda_1$ when excited with light of wavelengths $\lambda_1$.

4. An optical fiber as claimed in claim 3, the fiber additionally including a clear cladding between the core and said fluorescent cladding.

5. An optical fiber as claimed in claim 3 and adapted to sense temperature changes, wherein said cladding is in contact with said core and its index of refraction varies as a function of temperature to a greater extent than the variation of the index of refraction of the core.

6. A fiber optic thermometer, comprising:
(a) a temperature probe comprised of an optical fiber as claimed in claim 5;
(b) optical means including light source means and fiber optic means for injecting into said core interrogating light having wavelengths within an absorption band of said fluorescent dye, thereby generating at said cladding a fluorescence light having an intensity which varies as a function of the probe temperature;
(c) fiber optic means for directing a fraction of the intensity of said fluorescence light to photodetector means; and
(d) photodetector means for converting said fraction of the intensity of said fluorescence light into an electrical signal indicative of the probe temperature.

7. A fiber optic thermometer as claimed in claim 6 and adapted to measure temperature changes smaller than 0.1 kelvins, wherein the fiber probe has a sensing point with a bend threat for filling its numerical aperture, and wherein said cladding is coated at said sensing point with a coating which absorbs and removes the fluorescence light from the fiber generated at at least a fraction of the fiber length at said sensing point.

8. A device for sensing temperature changes, including:
(a) an optical fiber probe having a first end and a second end and comprising a core having an index of refraction $n_1$, a first cladding around said core having an index of refraction $n_2$ lower than $n_1$, and a second cladding around said first cladding having an index of refraction $n_3$ lower than $n_2$, the value of $n_2$ decreasing in a known manner with an increase in temperature at a greater rate than the decrease in the value of $n_1$ for the same temperature change;
(b) light source means for injecting interrogating light into said core and said first cladding at said first end of said fiber probe, the intensity of said interrogating light being distributed between said core and said first cladding, the relative distribution varying in a known manner with the probe temperature; and (c) optical means located at or near said second fiber end including photodetector and associated means for measuring the relative distribution of the intensity of said interrogating light between said core and said first cladding.

9. A device as claimed in claim 8 wherein the temperature coefficients of $n_2$ and $n_3$ are substantially similar.

10. A device for sensing temperature changes at a plurality of sensing points, comprising:

(a) an optical fiber as recited in claim 8 and disposed along a path including said sensing points;

(b) light source means for injecting interrogating light pulses of submicrosecond duration, a given intensity and wavelengths $\lambda_1$ into said core and said first cladding at one end of said fiber probe designated herein as the launch end, the intensity of said interrogating light being distributed between said core and said first cladding, the relative distribution varying in a known manner with the probe temperature;

(c) fiber optic means located at or near said launch end for directing a fraction of the intensity of the interrogating light backscattered from the fiber at said sensing points to photodetector means; and (d) photodetector and associated optical means located near said optical means for measuring the relative intensities of the pulses of light backscattered from said core and said first cladding at said temperature sensing points along the fiber.

11. A device including the optical fiber and light source means as claimed in claim 10, wherein said second cladding of said fiber has a fluorescent dye incorporated therein and so characterized that, when excited with said interrogating light pulses of wavelengths $\lambda_1$, it emits fluorescence light pulses including wavelengths $\lambda_2$ different from $\lambda_1$, the device additionally including means for measuring the intensities of the fluorescence pulses backscattered from said temperature sensing points along the fiber.

12. A device as claimed in claim 11 and additionally including means for comparing the intensities of said pulses of light of wavelengths $\lambda_1$ and said pulses of fluorescence light backscattered from the temperature sensing points along the fiber, the relative intensities of said pulses backscattered from a temperature sensing point being an indicator of the temperature of said point.

13. A device as claimed in claim 10 wherein the temperature coefficients of $n_2$ and $n_3$ are substantially similar.

14. A method for sensing temperature changes in an object or environment, including the steps of:

(a) placing an optical fiber probe having a proximal end and a distal end in thermal communication with said object or environment, said fiber probe comprising a core having an index of refraction $n_1$, a first cladding around said core having an index of refraction $n_2$ lower than $n_1$, and a second cladding around said first cladding having an index of refraction $n_3$ lower than $n_2$, the value of $n_2$ decreasing in a known manner with an increase in temperature at a greater rate than the decrease in the value of $n_1$ for the same temperature change;

(b) injecting interrogating light into said core and said first cladding at the proximal end of said fiber probe, the intensity of said interrogating light being distributed between said core and said first cladding, the relative distribution varying in a known manner with the probe temperature;

(c) selectively directing light propagating along said first cladding to photodetector means; and (d) measuring the intensity of said light propagating along said first cladding to said photodetector means.

15. A method as claimed in claim 14 wherein the temperature coefficients of $n_2$ and $n_3$ are substantially similar.

16. A method as claimed in claim 14 and adapted to sense temperature changes at a plurality of sensing points, wherein said fiber probe is disposed along a path including said locations and said interrogating light is injected into said core and said first cladding is in the form of short pulses of submicrosecond duration, the method additionally including the steps of:

(a) directing at least a fraction of the intensity of light backscattered from each sensing point along the fiber probe to photodetector means; and (b) measuring the relative intensities of the pulses of light backscattered from said core and said first cladding at said temperature sensing points along the fiber.

17. An optical fiber probe having a first end and a second end and comprising a core having an index of refraction $n_1$, a first cladding around said core having an index of refraction $n_2$ lower than $n_1$, and a second cladding around said first cladding having an index of refraction $n_3$ lower than $n_2$, the value of $n_2$ decreasing in a known manner with an increase in temperature at a greater rate than the decrease in the value of $n_1$ for the same temperature change.

18. An optical fiber as claimed in claim 17 wherein said second cladding has a fluorescent dye incorporated therein.

19. An optical fiber as claimed in claim 17 wherein the temperature coefficients of $n_2$ and $n_3$ are substantially similar.

* * * * *